(12) United States Patent
Olsen et al.

(10) Patent No.: US 8,123,770 B2
(45) Date of Patent: Feb. 28, 2012

(54) ANGIOPLASTY CUTTING DEVICE AND METHOD FOR TREATING A STENOTIC LESION IN A BODY VESSEL

(75) Inventors: Kian Olsen, Bloomington, IN (US); Mark J. Hiatt, Ellettsville, IN (US); Michael W. Hardert, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 741 days.

(21) Appl. No.: 11/591,050

(22) Filed: Nov. 1, 2006

(65) Prior Publication Data

US 2007/0106215 A1 May 10, 2007

Related U.S. Application Data

(60) Provisional application No. 60/732,260, filed on Nov. 1, 2005.

(51) Int. Cl.
*A61B 17/22* (2006.01)

(52) U.S. Cl. .................................. 606/159; 606/191

(58) Field of Classification Search ............ 606/159, 606/167, 170–171, 178, 179, 180, 191, 192, 606/194, 198; 604/103.02, 103.03, 103.05, 604/103.06, 103.07, 103.08; 623/1.11, 1.15
See application file for complete search history.

(56) References Cited

U.S. PATENT DOCUMENTS

| | | | |
|---|---|---|---|
| 4,535,757 A | 8/1985 | Webster, Jr. | |
| 4,729,763 A | 3/1988 | Henrie | |
| 4,877,030 A | 10/1989 | Beck et al. | |
| 4,886,061 A | 12/1989 | Fischell et al. | |
| 4,898,575 A | 2/1990 | Fischell et al. | |
| 4,921,479 A * | 5/1990 | Grayzel | ............ 604/509 |
| 5,030,201 A | 7/1991 | Palestrant | |
| 5,047,040 A | 9/1991 | Simpson et al. | |
| 5,078,723 A | 1/1992 | Dance et al. | |
| 5,080,660 A | 1/1992 | Buelna | |
| 5,181,920 A | 1/1993 | Mueller et al. | |
| 5,192,291 A | 3/1993 | Pannek, Jr. | |
| 5,192,307 A * | 3/1993 | Wall | ............... 623/1.2 |
| 5,196,024 A | 3/1993 | Barath | |
| 5,209,749 A | 5/1993 | Buelna | |
| 5,224,945 A | 7/1993 | Pannek, Jr. | |
| 5,224,949 A | 7/1993 | Gomringer et al. | |
| 5,320,634 A * | 6/1994 | Vigil et al. | ............ 606/159 |
| 5,336,178 A * | 8/1994 | Kaplan et al. | ............ 604/509 |
| 5,372,601 A | 12/1994 | Lary | |
| 5,409,454 A | 4/1995 | Fischell et al. | |

(Continued)

FOREIGN PATENT DOCUMENTS

EP 0117519 9/1984

*Primary Examiner* — Tuan Nguyen
*Assistant Examiner* — David Eastwood
(74) *Attorney, Agent, or Firm* — Brinks Hofer Gilson & Lione (57) ABSTRACT

An integrally formed angioplasty cutting device for balloon angioplasty of a stenotic lesion in a body vessel. The device comprises a distal collar and a proximal collar. The device further comprises at least one strut integrally formed with the distal collar and the proximal collar. At least one of the collars has a slot formed therethrough defining a C-shaped configuration. The strut is configured to be disposed at the stenotic lesion to engage the stenotic lesion for dilatation of the body vessel during angioplasty.

18 Claims, 8 Drawing Sheets

U.S. PATENT DOCUMENTS

| | | |
|---|---|---|
| 5,411,478 A | 5/1995 | Stillabower |
| 5,431,673 A | 7/1995 | Summers et al. |
| 5,441,510 A | 8/1995 | Simpson et al. |
| 5,450,843 A | 9/1995 | Moll et al. |
| 5,505,725 A | 4/1996 | Samson |
| 5,522,790 A * | 6/1996 | Moll et al. .................... 600/204 |
| 5,556,408 A | 9/1996 | Farhat |
| 5,569,277 A | 10/1996 | Evans et al. |
| 5,571,087 A | 11/1996 | Ressemann et al. |
| 5,575,771 A | 11/1996 | Walinsky |
| 5,609,628 A | 3/1997 | Keranen |
| 5,616,149 A * | 4/1997 | Barath .......................... 606/159 |
| 5,628,746 A | 5/1997 | Clayman |
| 5,722,979 A | 3/1998 | Kusleika |
| 5,728,129 A | 3/1998 | Summers |
| 5,792,158 A | 8/1998 | Lary |
| 5,797,935 A * | 8/1998 | Barath .......................... 606/159 |
| 5,904,679 A | 5/1999 | Clayman |
| 5,921,958 A | 7/1999 | Ressemann et al. |
| 5,941,869 A | 8/1999 | Patterson et al. |
| 6,036,708 A | 3/2000 | Sciver |
| 6,123,718 A | 9/2000 | Tu et al. |
| 6,165,187 A | 12/2000 | Reger |
| 6,254,608 B1 | 7/2001 | Solar |
| 6,264,672 B1 * | 7/2001 | Fisher .......................... 606/200 |
| 6,306,151 B1 | 10/2001 | Lary |
| 6,508,824 B1 | 1/2003 | Flaherty et al. |
| 6,629,953 B1 | 10/2003 | Boyd |
| 6,632,231 B2 | 10/2003 | Radisch, Jr. |
| 6,656,174 B1 * | 12/2003 | Hegde et al. .................... 606/41 |
| 2001/0051810 A1 | 12/2001 | Dubrul et al. |
| 2002/0026217 A1 * | 2/2002 | Baker et al. .................... 606/223 |
| 2002/0099434 A1 * | 7/2002 | Buscemi et al. .............. 623/1.11 |
| 2003/0028212 A1 | 2/2003 | Saab |
| 2003/0040754 A1 | 2/2003 | Mitchell et al. |
| 2003/0114868 A1 | 6/2003 | Fischell et al. |
| 2003/0144677 A1 | 7/2003 | Lary |
| 2003/0153870 A1 | 8/2003 | Meyer et al. |
| 2004/0111108 A1 | 6/2004 | Farnan |
| 2004/0122457 A1 * | 6/2004 | Weber .......................... 606/159 |
| 2004/0143287 A1 * | 7/2004 | Konstantino et al. ......... 606/194 |
| 2004/0193196 A1 | 9/2004 | Appling et al. |
| 2004/0243158 A1 | 12/2004 | Konstantino et al. |
| 2005/0021071 A1 | 1/2005 | Konstantino et al. |
| 2005/0033334 A1 | 2/2005 | Santra et al. |
| 2005/0090845 A1 | 4/2005 | Boyd |
| 2005/0090846 A1 | 4/2005 | Pedersen et al. |

* cited by examiner

ANGIOPLASTY CUTTING DEVICE AND METHOD FOR TREATING A STENOTIC LESION IN A BODY VESSEL

CROSS-REFERENCE TO RELATED APPLICATIONS

This application claims the benefit of U.S. Provisional Application no. 60/732,260, filed on Nov. 1, 2005, entitled "INTEGRALLY FORMED ANGIOPLASTY CUTTING DEVICE AND METHOD FOR TREATING A STENOTIC LESION IN A BODY VESSEL," the entire contents of which are incorporated herein by reference.

BACKGROUND OF THE INVENTION

The present invention relates to medical devices. More particularly, the present invention relates to angioplasty cutting devices and methods for treating a stenotic lesion in a body vessel.

Vascular diseases, such as coronary artery disease, are common diseases. Such diseases are caused by stenotic lesions narrowing in a body vessel within the vasculature. Generally, carotid artery stenosis is the narrowing of the carotid arteries, the main arteries in the neck that supply blood to the brain. Carotid artery stenosis (also called carotid artery disease) is a relatively high risk factor for ischemic stroke. The narrowing is usually caused by plaque build-up in the carotid artery. Plaque forms when cholesterol, fat and other substances form in the inner lining of an artery. This formation is called atherosclerosis.

Currently, depending on the degree of stenosis and the patient's overall condition, carotid artery stenosis can usually be treated with surgery. The procedure is (with its inherent risks) called carotid endarterectomy, which removes the plaque from the arterial walls. Carotid endarterectomy has proved to benefit patients with arteries stenosed by about 70% or more. For people with arteries narrowed less than 50%, an anti-clotting agent may be prescribed to reduce the risk of ischemic stroke.

Carotid angioplasty is another treatment for carotid artery stenosis. This treatment uses balloons and/or stents to open a narrowed artery. Carotid angioplasty is a procedure that can be performed via a standard percutaneous transfemoral approach with the patient anesthetized using light intravenous sedation. At the stenosis area, an angioplasty balloon is delivered to predilate the stenosis in preparation for stent placement. The balloon is then removed and exchanged via catheter for a stent delivery device. Once in position, a stent is deployed across the stenotic area. If needed, an additional balloon can be placed inside the deployed stent for post-dilation to make sure the struts of the stent are pressed firmly against the inner surface of the vessel wall.

However, an ongoing problem with angioplasty is that the arterial blockage may return, usually within about 6 months. It is thought that the mechanism of this phenomenon, called "restenosis," is not the progression of the arterial disease, but rather the body's immune system response to the angioplasty. At this point, a repeat procedure may need to be performed.

Thus, there is a need to provide a way for decreasing the likelihood of restenosis without the inherent risks of surgery.

BRIEF SUMMARY OF THE INVENTION

The present invention generally provides an improved cutting assembly, an integrally formed cutting device, and an improved method for treating a stenotic lesion of a body vessel, decreasing the likelihood of restenosis without the inherent risks of surgery. Embodiments of the present invention provide a simple, efficient and cost effective device and a way of treating atherosclerosis and stenosis of a body vessel. For example, the integrally formed cutting device of the present invention provides an effective, efficient way of breaking plaque of a stenotic lesion while having the capability of using various sizes of angioplasty balloons.

One embodiment of the present invention is an integral angioplasty cutting device for balloon angioplasty of a stenotic lesion in a body vessel. The device is an integral member and comprises a distal collar configured to be disposed at the distal end of the stenotic lesion relative to the device. The device further comprises at least one strut integral with the distal collar and proximally extending therefrom. The at least one strut is configured to be disposed at the stenotic lesion to engage the stenotic lesion for dilatation of the body vessel during angioplasty. The device further comprises a proximal collar configured to be disposed at the proximal end of the stenotic lesion relative to the device. The at least one strut is integral with the proximal collar. In this embodiment, the at least one of the distal collar and proximal collar has a slot formed therethrough to define a C-shaped configuration. The C-shaped configuration allows the device to be coaxially adaptable about an expandable balloon for angioplasty. The C-shaped configuration of one of the collar allows the device to be fastened on the expandable balloon, thereby minimizing the cross-sectional profile of the device.

Yet another embodiment of the present invention is an atherosclerosis cutting apparatus for treatment of a stenotic lesion in a body vessel. The apparatus comprises a balloon catheter having a tubular body and an expandable balloon attached to and in fluid communication with the tubular body for angioplasty at the stenotic lesion. The expandable balloon has distal and proximal portions. The apparatus further includes the integral angioplasty cutting device coaxially adaptable about the expandable balloon for angioplasty of the stenotic lesion in the body vessel.

In another example, the present invention provides a method for treatment of a stenotic lesion in a body vessel. The method comprises percutaneously introducing an expandable balloon at a stenotic lesion in a body vessel and disposing the integral atherosclerosis cutting device coaxially about the expandable balloon for angioplasty of the stenotic lesion in the body vessel. The method further includes fracturing the stenotic lesion in the body vessel on each radial plane of fracture by expanding the balloon and the device on the stenotic lesion.

Further objects, features, and advantages of the present invention will become apparent from consideration of the following description and the appended claims when taken in connection with the accompanying drawings.

BRIEF DESCRIPTION OF THE DRAWINGS

FIG. 7b is a side view of the assembly of FIG. 7a;

DETAILED DESCRIPTION OF THE INVENTION

The present invention generally provides an improved cutting assembly, an integrally formed cutting device, and an improved method for treating a stenotic lesion of a body vessel. Embodiments of the present invention provide a more simple, efficient and cost effective way of treating atherosclerosis and stenosis of a body vessel. For example, the integrally formed cutting device includes distal and proximal collars having a C-shaped configuration and being integrated with a cutting body extending integrally therebetween. The device is configured to be disposed about one of a number of various-sized expandable balloons of a balloon catheter for angioplasty. The cutting body has one or a plurality of struts which expand as the expandable balloon is inflated. Each strut defines a focal point or a radial plane of fracture on the stenotic lesion whereat lacerations on the stenotic lesion are formed. Upon contact with the stenotic lesion, the struts break the plaque in a relatively organized fashion, lessening the likelihood of restenosis of the body vessel.

Figure 1:
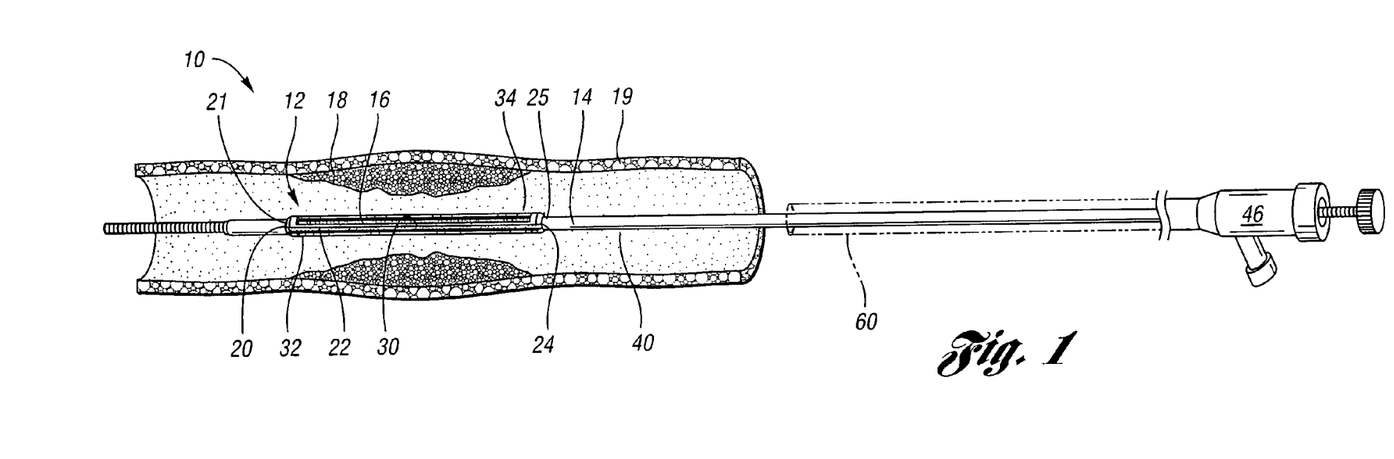
FIG. 1 is an environmental view of an integrally formed atherosclerosis cutting device in a collapsed state in a body vessel in accordance with one embodiment of the present invention.
Figure 2:
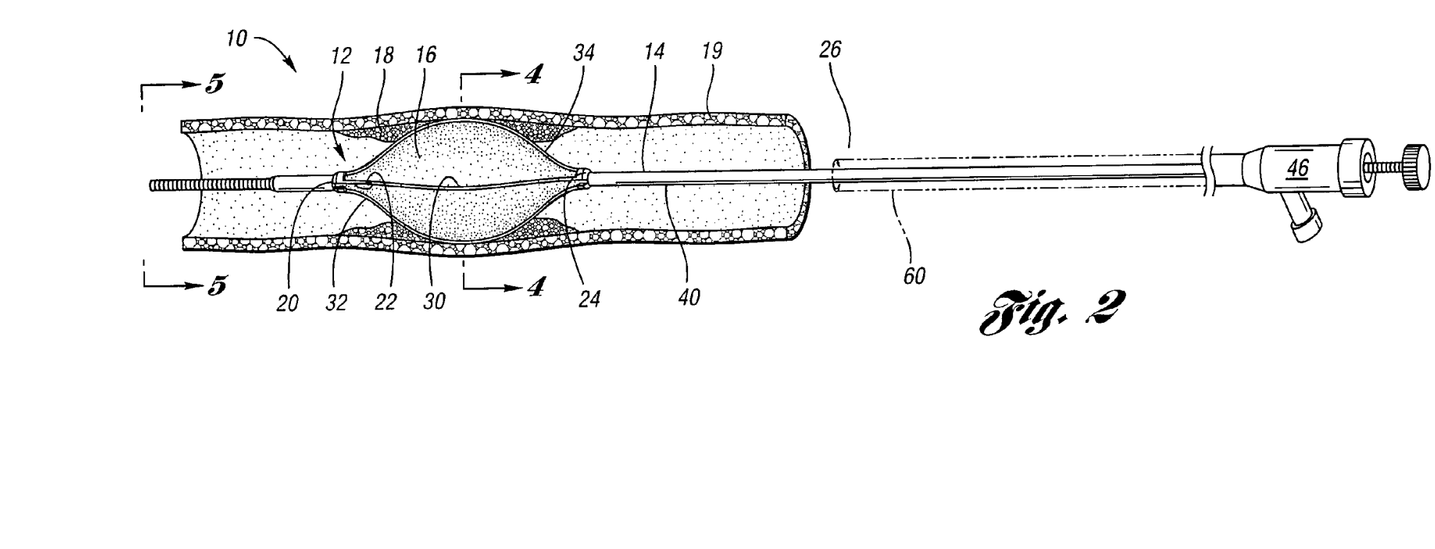
FIG. 2 is another environmental view of the integrally formed cutting device in an expanded state for balloon angioplasty of the stenotic lesion in the body vessel.

FIG. 1 illustrates an angioplasty cutting assembly or apparatus 10 having an expandable balloon 16 and implementing an integrally formed atherosclerosis cutting device 12 in accordance with one embodiment of the present invention. As depicted in FIGS. 1 and 2, the cutting assembly 10 includes a balloon catheter 14 about which the device 12 is disposed. As shown, the balloon catheter 14 comprises an expandable balloon 16 for angioplasty treatment of a stenotic lesion 18 of a body vessel 19. The balloon catheter 14 is configured to be cooperable with the device 12 during the procedure. As shown, the device 12 is disposable about the expandable balloon 16 of the assembly 10. As the balloon is inflated, the device 12 expands to engage the stenotic lesion 18 of the body vessel 19.

FIG. 1 further depicts the assembly 10 in a collapsed or an unexpanded state that the device 12 takes on during delivery and retrieval thereof. FIG. 2 shows the assembly 10 in an expanded state that the device 12 takes on during angioplasty. The expandable balloon 16 of the assembly 10 may be inflated and deflated by any suitable means, e.g., by introducing saline into the expandable balloon 16 as known in the art.

Figure 3A:
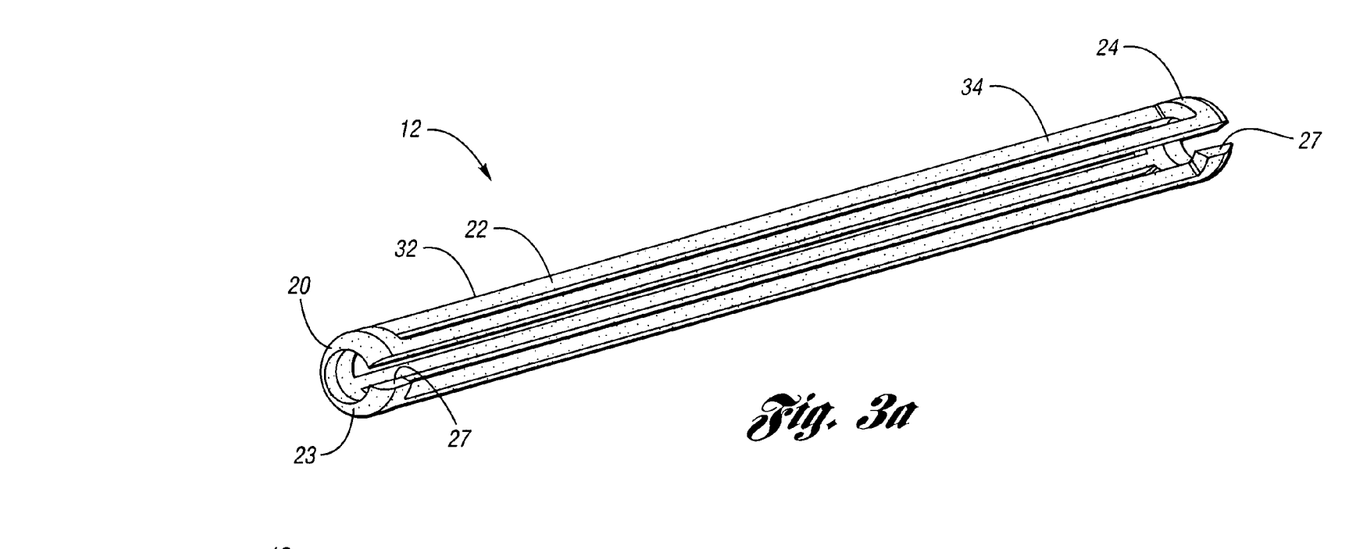
FIG. 3a is a perspective view of the cutting device depicted in FIGS. 1 and 2.
Figure 3B:
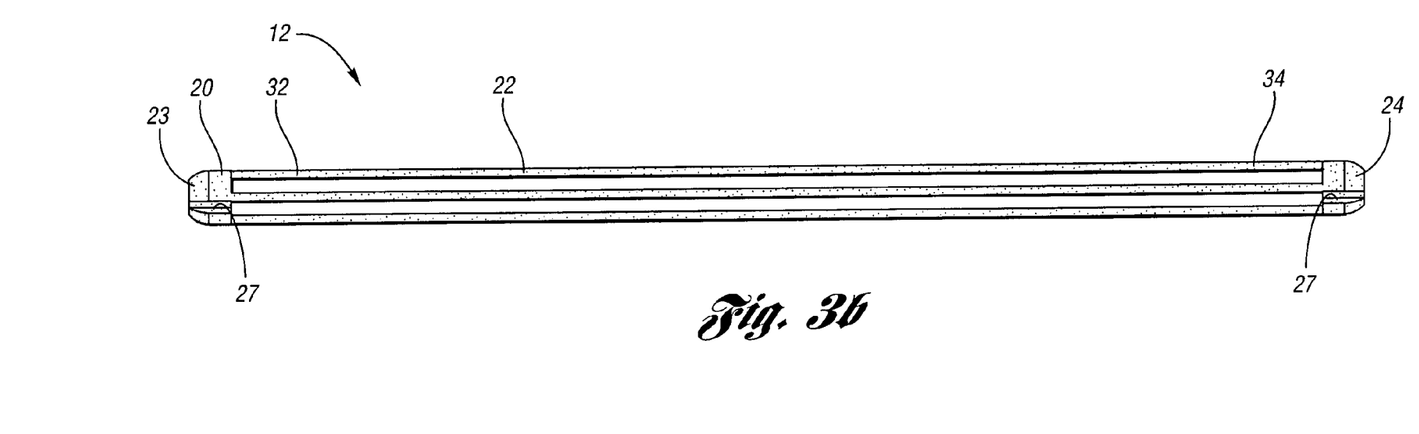
FIG. 3b is a side view of the cutting device.

FIGS. 1-3b generally illustrate the device 12 in this embodiment being a one-piece member or an integral device. As shown, the device 12 comprises a distal collar 20, a cutting body 22 integrally extending from the distal collar 20, and a proximal collar 24 to which the cutting body 22 integrally extends. FIGS. 3a and 3b depict the distal collar 20 having a tapered, atraumatic distal tip 23 for enhanced guidance and reduced trauma in the body vessel of a patient. For enhanced atraumatic performance, the distal tip 23 may be coated with soft, hydrophilic material such as low density polyethylene, polypropylene, polytetrafluoroethylene (PTFE) or any other suitable material or mixtures thereof.

Preferably, at least one of the distal collar 20 and the proximal collar 24 of the cutting device 12 has a slit or slot formed therethrough defining a C-shaped configuration of the device 12. As shown, the C-shaped configuration is formed longitudinally relative to the device 12, defining an opening 27. The C-shaped configuration is formed longitudinally relative to the device, allowing the collar to be fastened about the expandable balloon for attachment to the assembly. In this embodiment, the openings 27 may have a size of between about 0.01 mm (about 0.0004 in) and 1 mm (about 0.04 in). Each of the openings 27 allows its respective collar 20 or 24 to be attached or fastened about the balloon catheter or expandable balloon for attachment to the assembly 10. Preferably, both of the distal and proximal collars 20, 24 include the C-shaped configuration. The C-shaped configuration formed on each or both of the collars 20, 24 further allows device 12 to be manufactured at a reduced cross-sectional profile. In turn, this reduces cross-sectional profile of the balloon catheter and expandable balloon, thereby lowering the overall minimum cross-sectional profile of the assembly.

The cutting body 22 defines at least one radial plane of fracture A (see FIG. 4) in the body vessel 19 during angioplasty. As shown, the distal collar 20 is preferably ring or collar shaped and located at the distal portion of the cutting device 12. In this embodiment, the distal collar 20 is configured to be disposed about and adjacent the distal end 21 of the expandable balloon 16 relative to the device 12.

As will be discussed in greater detail below, the device of this embodiment is an integral member formed from a single solid tube of any suitable material discussed below. Known manufacturing techniques may be implemented to form the distal collar, the cutting body, and the proximal collar of the device. For example, laser cutting or etching may be used to form a tubular member to the integral device.

In this embodiment, the cutting body 22 is defined by a plurality of struts 30 integral with the distal collar 20 and integrally extending to the proximal collar 24. However, it is to be noted that the cutting body 22 may include merely one strut integrally extending from the distal collar 20 to the proximal collar 24. Each strut 30 is preferably integral with the distal collar 20 and extends proximally longitudinally therefrom. Preferably, each strut 30 has a first portion 32 and a second portion 34. In this embodiment, the first portion 32 is a distal portion, and the second portion 34 is a proximal portion relative to the device 12. The cutting body 22 is configured to be radially expandable with the expandable balloon to engage the stenotic lesion 18 for dilatation of the body vessel 19 during angioplasty. As shown, each strut 30 is configured to be placed at the stenotic lesion 18 and to extend longitudinally along the length of the stenotic lesion 18.

The device 12 may be a tubular member comprised of any suitable material such as a superelastic material, stainless steel wire, cobalt-chromium-nickel-molybdenum-iron alloy, cobalt-chrome alloy, or Nitinol. By implementing known techniques, e.g., laser etching, the tubular member may be formed in the shape as depicted in FIGS. 3a and 3b, to define the single member integral device. Moreover, it is understood that the device 12 may be formed of any other suitable material that will result in a self-opening or self-expanding device, such as shape memory alloys. Shape memory alloys have the desirable property of becoming rigid, that is, returning to a remembered state, when heated above a transition temperature.

In this embodiment, each of the distal collar 20 and the proximal collar 24 has a longitudinal length of between about 1 millimeter (mm) (about 0.04 inch) and 3 mm (about 0.12 in), and preferably about 2 mm (about 0.08 in). Each of the distal collar 20 and the proximal collar 24 may have an inner diameter (ID) of between about 1.3 mm (about 0.05 in) and 1.6 mm (about 0.06 in), and preferably 1.5 mm (0.06 in). Moreover, each of the distal collar 20 and the proximal collar 24 may have an outer diameter (OD) of between about 1.5 mm (about 0.05 in) and 3 mm (about 0.12 in), and preferably 2 mm (about 0.08 in). Each of the distal collar 20 and the proximal collar 24 may have a constant OD along the longitudinal axis. In this embodiment, each of the struts 30 has an OD of between about 0.25 mm (about 0.01 in) and 0.76 mm (about 0.03 in), and preferably about 0.36 mm (about 0.014 in). Each of the struts 30 has a length of between about 40 mm (about 1.5 in) and 60 mm (about 2.3 in), and preferably 50 mm (about 1.9 in). A radial distance between the longitudinal axis and at least one of the struts 30 in the collapsed configuration is at least the radius of the proximal collar 20 and the distal collar 24.

In this embodiment, the cutting body 22 comprises four struts 30 that are formed to be spaced relatively equally apart at about 90 degrees from each adjacent strut 30. However, it is to be understood that the number of struts may vary and that the struts may be spaced apart from each other in any other manner without falling beyond the scope of the present invention.

Preferably, each strut defines a focal point or a radial plane of fracture A whereat lacerations to the stenotic lesion 18 are formed during angioplasty. That is, the struts 30 cut the plaque of the lesion at focal points to provide the radial planes of fracture A to the lesion, thereby dilating the body vessel 19. During angioplasty, each strut 30 of the cutting body 22 expands along its respective radial plane of fracture A to engage the stenotic lesion 18 in the body vessel 19. Upon contact with the lesion, the struts 30 break the plaque in a relatively organized fashion. It has been found that, as the expandable balloon pushes the lesion radially outwardly, the struts cut and allow the plaque to be folded for further dilatation of the body vessel. Furthermore, trauma to the lesion caused by the struts 30 results in relatively organized lacerations that minimize or lessen the likelihood of restenosis of the body vessel. Thus, the lacerations formed on the lesion allow for a relatively more effective treatment of stenosis.

The struts 30 may be made of a rigid material, a superelastic material or a shape memory material. For example, the struts 30 may be made of metals (e.g., stainless steel), Nitinol, or a polymeric material (e.g., high density polyethylene or polypropylene). Preferably, each of the struts 30 has a diameter of between about 0.014 inch and 0.018 inch.

As mentioned above, each strut 30 is preferably integral with the distal collar 20 and the proximal collar 24 such that the device 12 is a one-piece device configured to be radially placed about the expandable balloon 16. Thus, each first portion 32 is integral with the distal collar 20 and extends to the second portion 34 which is integral with the proximal collar 24 defining the integrally formed cutting device 12. As mentioned above, the device may be integrally formed by manufacturing the device from a tubular member via known manufacturing techniques such as laser etching and cutting. As shown in FIGS. 3a and 3b, the struts 30 integrally extend from the distal collar 20 and are integral with the proximal collar 24. The distal collar 20 is configured to be disposed about and adjacent the distal end 21 of the expandable balloon 16 relative to the device 12. The proximal collar 24 is configured to be disposed about and adjacent the proximal end 25 of the expandable balloon 16 relative to the device 12.

Figure 4:
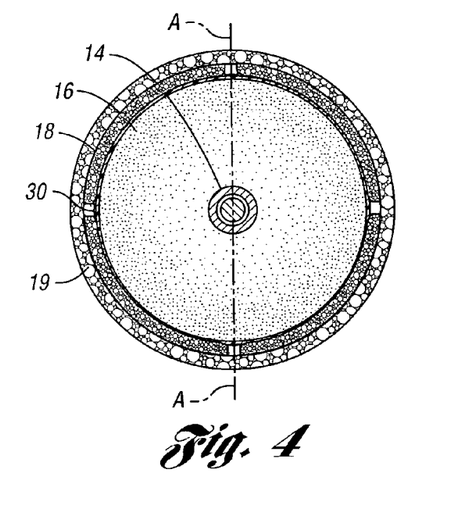
FIG. 4 is a cross-sectional view of the cutting device of FIG. 2 taken along line 4-4.
Figure 5:
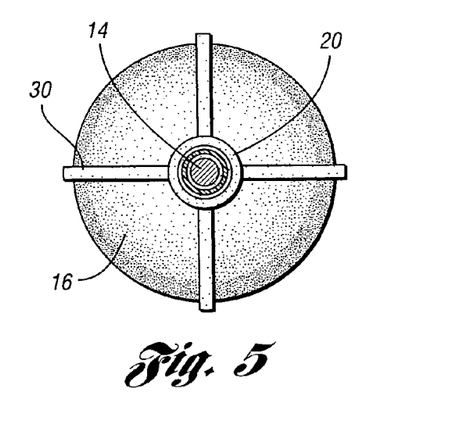
FIG. 5 is an end view of the cutting device of FIG. 2.

The condition of the device 12 is dictated by the condition of the expandable balloon 16 of the assembly 10. FIGS. 4 and 5 depict cross-sectional and end views of the device 12 taken along lines 4-4 and 5-5 of FIG. 2, respectively. As shown, the expansion of the struts 30 of the device are dictated by the inflation of the angioplasty balloon such that each strut expands along its respective radial plane of fracture to contact and fracture the stenotic lesion 18, thereby lessening the likelihood of restenosis.

Figure 6A:
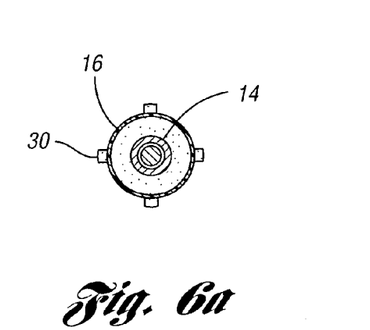
FIG. 6a is a cross-sectional view of the cutting device in the collapsed state.

FIGS. 6a-6d depict states that the device 12 takes on during a stenotic procedure as the expandable balloon 16 is inflated to engage the struts 30 with the stenotic lesion 18. FIG. 6a illustrates the device 12 in a collapsed state. In the collapsed state, the device 12 and assembly 10 may be delivered to and retrieved from a stenotic lesion 18. In this embodiment, the outer diameter of the expandable balloon is about 0.3 to 3 millimeters (mm).

Figure 6B:
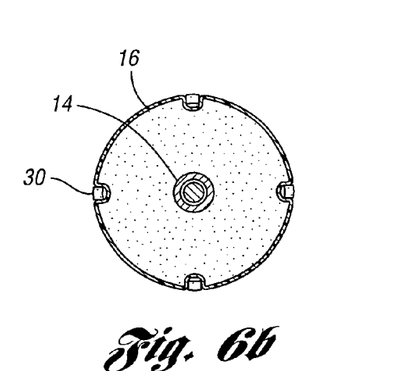
FIGS. 6b-6d are cross-sectional views of the cutting device in transition states during inflation of the expandable balloon.
Figure 6C:
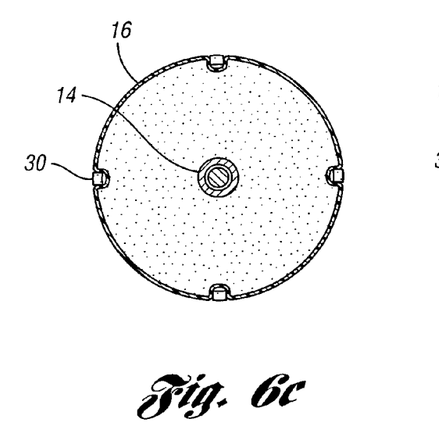
Figure 6D:
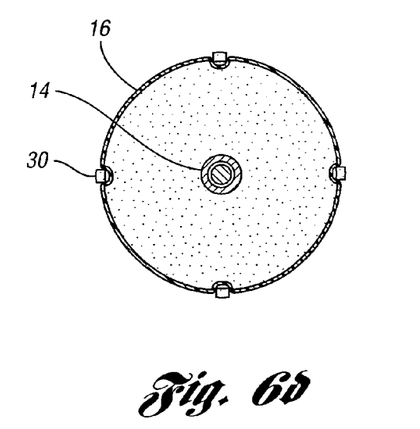

FIGS. 6b-6d illustrate the device 12 in transition states during inflation of the expandable balloon 16. During the transition states, the device 12 may begin contacting the stenotic lesion 18. In this embodiment, in FIG. 6b, the outer diameter of the expandable balloon is about 3 to 6 mm. In FIGS. 6c and 6d, the outer diameter of the expandable balloon is about 3 to 8 mm.

Figure 6E:
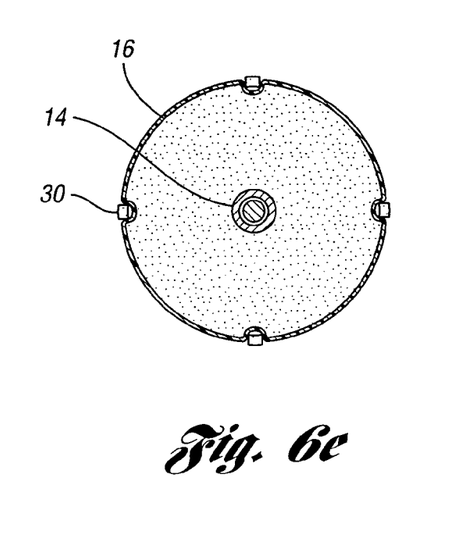
FIG. 6e is a cross-sectional view of the cutting device in the expanded state.

FIG. 6e depicts the device 12 in an expanded state as the balloon inflation is completed. In the expanded state, the struts 30 of the device 12 are preferably in contact or relatively near contact with the vessel wall and have fractured the stenotic lesion 18. The organized fracturing and trauma to the stenotic lesion 18 provides a lessened likelihood of restenosis of the body vessel. In this embodiment, the outer diameter of the expandable balloon is about 3 to 10 mm.

Figure 7A:
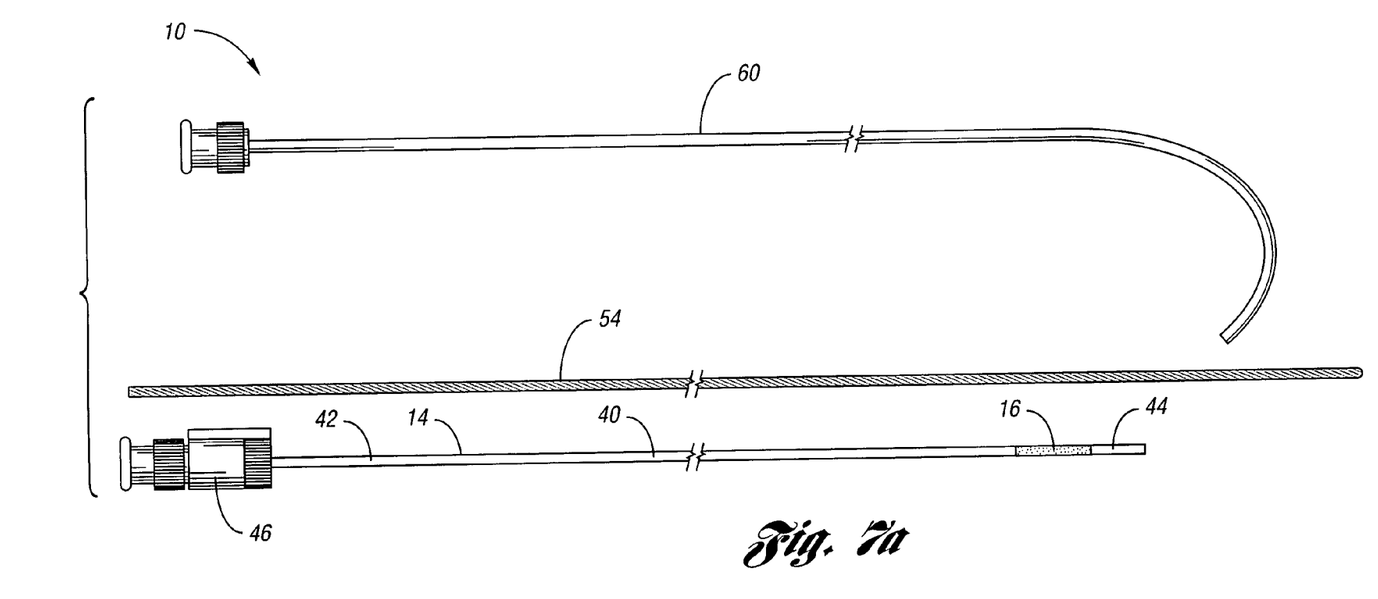
FIG. 7a is an exploded view of an assembly implementing the cutting device in accordance with one embodiment of the present invention.
Figure 7B:
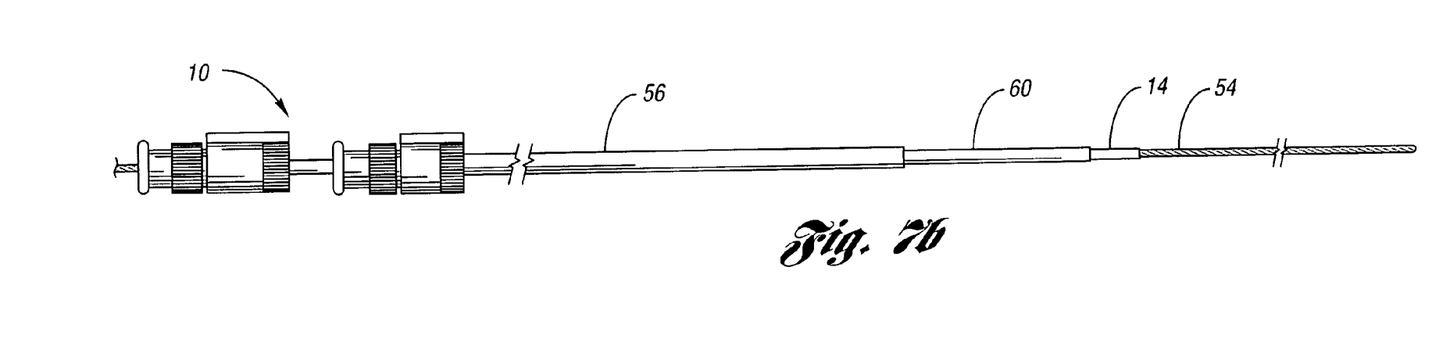

FIGS. 7a-7b depict a cutting assembly 10 that implements the cutting device 12 for treating a stenotic lesion 18 of a body vessel in accordance with one embodiment of the present invention. As shown, the assembly 10 includes the balloon catheter 14 having a tubular body 40 portion and an expandable balloon 16 disposed thereon. The expandable balloon 16 is preferably attached to and in fluid communication with the tubular body 40 for angioplasty at the stenotic lesion 18. The device 12 is configured to be disposed about the expandable balloon 16 for deployment at the stenotic lesion 18. The device 12 is preferably placed about the angioplasty balloon of the angioplasty catheter prior to insertion into the vasculature.

Generally, the balloon catheter 14 has a proximal end 42, a distal end 44, and a plastic adapter or hub 46 to receive assembly 10 to be advanced therethrough. The hub 46 is in fluid communication with the balloon for fluid to be passed therethrough for inflation and deflation of the balloon during angioplasty. In one embodiment, the balloon catheter 14 may include an outer lumen and an inner lumen. The outer lumen is preferably in fluid communication with the expandable balloon 16 for inflating and deflating the balloon. The inner lumen is formed therethrough for percutaneous guidance through the body vessel. The balloon catheter 14 is preferably made of a soft, flexible material such as a silicone or any other suitable material. In this embodiment, the inside diameter of the balloon catheter 14 may range between 0.010 and 0.027 inch.

The size of the expandable balloon 16 may also vary. For example, the balloon size may range between about 1 and 10 millimeters in diameter. The expandable balloon 16 has distal and proximal portions. The expandable balloon 16 may be made of any suitable material such as low density polymer material (e.g., polyethylene or polypropylene) or polyvinyl chloride (PVC).

The assembly 10 further includes a wire guide 54 which via an introducer sheath 56 (discussed in greater detail below) is percutaneously inserted to provide a path for the balloon catheter 14 within the vasculature of a patient. The balloon catheter 14 is configured to be disposed about the wire guide 54 for percutaneous guidance through the vasculature. The size of the wire guide 54 is based on the inside diameter of the introducer sheath 56.

As mentioned above, the assembly 10 further includes a polytetrafluoroethylene (PTFE) introducer sheath 56 for percutaneously introducing the wire guide 54 and the balloon catheter 14 in vasculature. Of course, any other suitable material may be used without falling beyond the scope or spirit of the present invention. The introducer sheath 56 is percutaneously inserted into the vasculature of the patient. The sheath may have a size of about 3-French to 8-French and allows the balloon catheter 14 to be inserted therethrough to the deployment location in the body vessel. In one embodiment, the sheath receives the balloon catheter 14 and the device 12, and provides stability thereto at the deployment location.

The assembly 10 may further include an outer catheter 60 disposed co-axially about the balloon catheter 14 and within the introducer sheath 56. As shown, the outer catheter 60 is preferably configured to house the balloon catheter 14 and the device 12 during delivery and retrieval thereof to and from the stenotic lesion 18. The outer catheter 60 is preferably advanced with the balloon catheter 14 and the device 12 to the deployment location. When the distal end of the expandable balloon 16 of the balloon catheter 14 is placed across the stenotic lesion 18 in the body vessel, the expandable balloon 16 may then be inflated preferably with saline. For deployment of the expandable balloon 16 and the cutting device 12, the outer catheter 60 is then retracted to expose the device 12 and angioplasty balloon at the stenotic lesion 18. The angioplasty balloon is inflated, and both the device 12 and balloon expands to break plaque of the stenotic lesion 18.

It is to be understood that the assembly 10 described above is merely one example of an assembly 10 that may be used to deploy the capturing device 12 in a body vessel. Of course, other apparatus, assemblies, and systems may be used to deploy any embodiment of the capturing device 12 without falling beyond the scope or spirit of the present invention.

Figure 8:
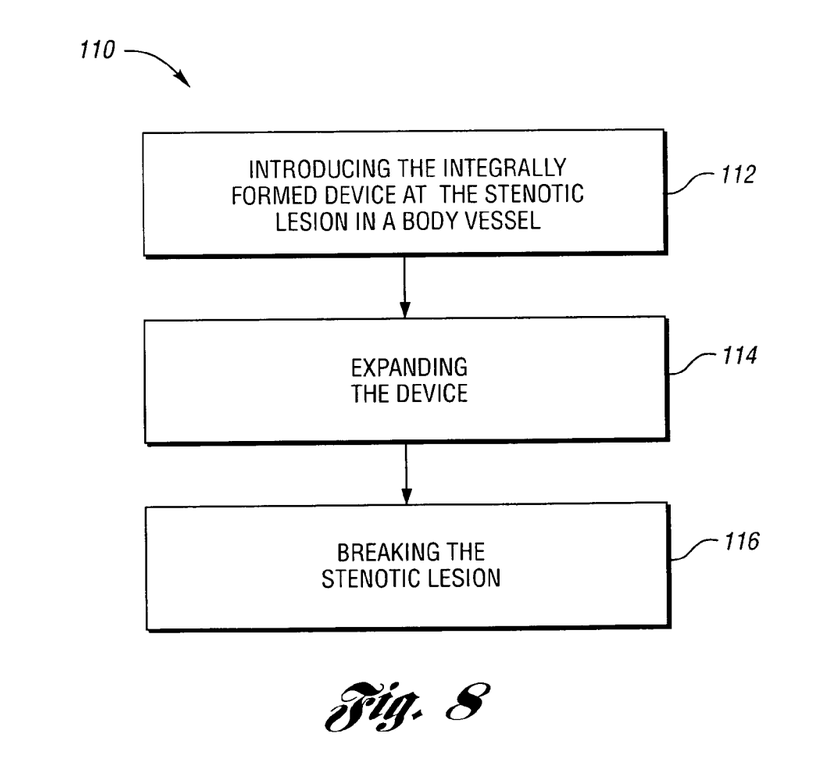
FIG. 8 is a flowchart depicting one method of treating a stenotic lesion in a body vessel using the atherosclerosis cutting device.
Figure 9:
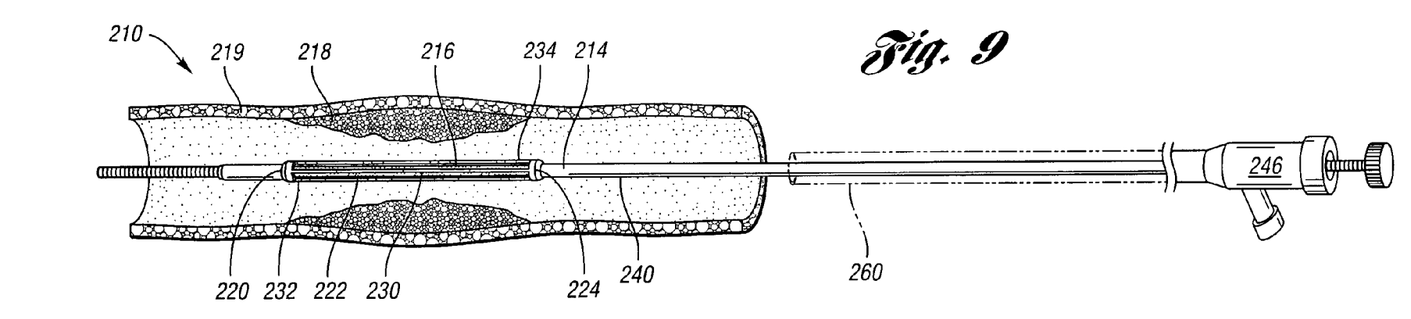
FIG. 9 is an environmental view of an integrally formed atherosclerosis cutting device in a collapsed state within a body vessel in accordance with another embodiment of the present invention.
Figure 10:
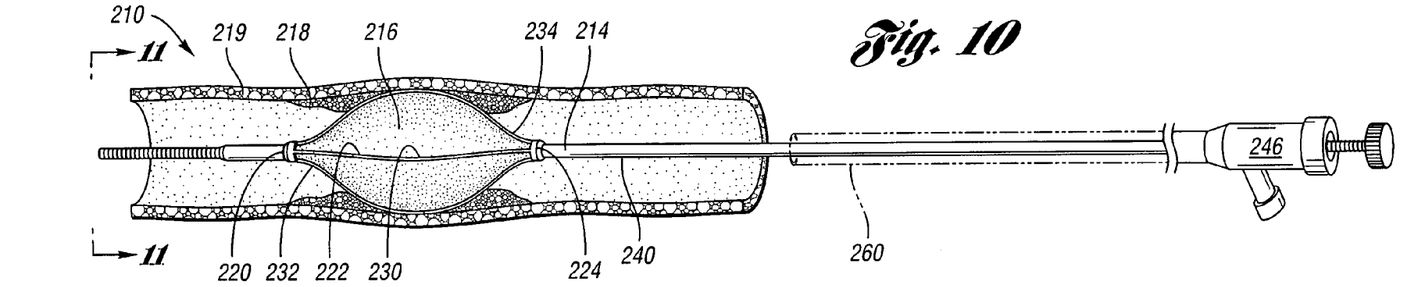
FIG. 10 is another environmental view of the integrally formed cutting device of FIG. 9 in an expanded state for balloon angioplasty of the stenotic lesion within the body vessel.
Figure 11:
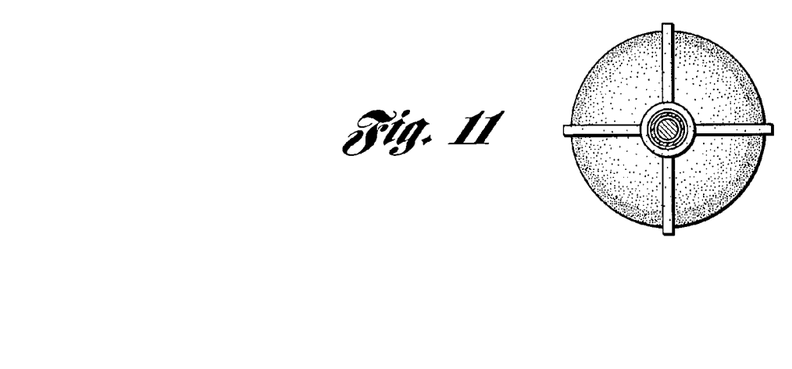
FIG. 11 is an end view of the cutting device in FIG. 10.
Figures 12, 13A:
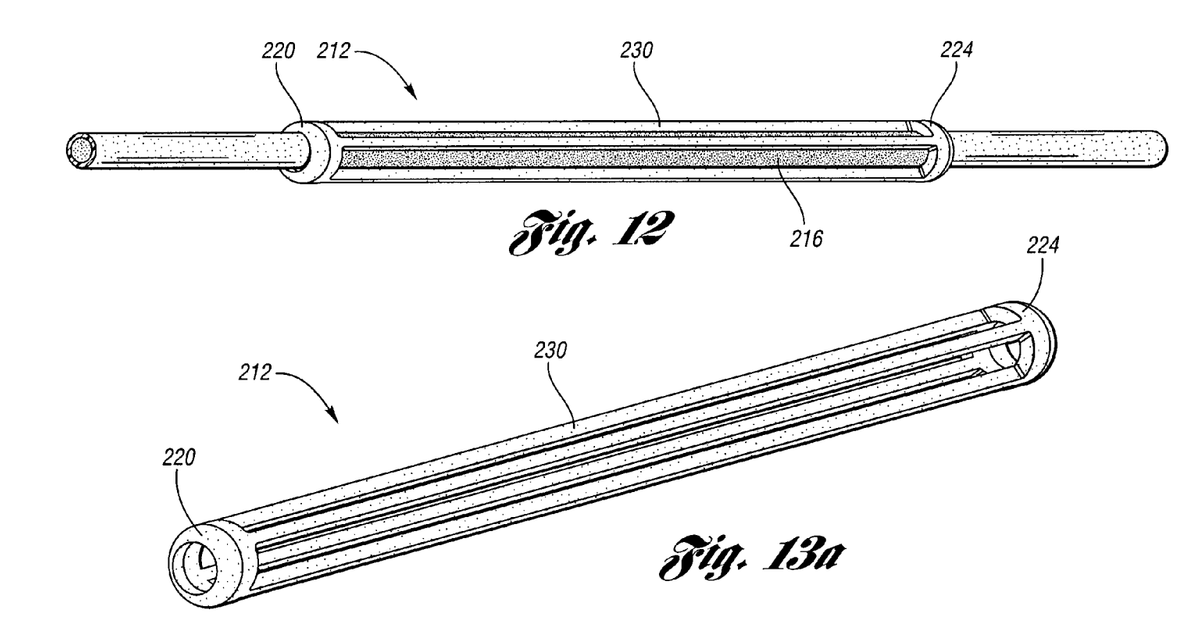
FIG. 12 is an enlarged view of the cutting device in FIG. 10.
FIG. 13a is a perspective view of the cutting device depicted in FIGS. 9 and 10.
Figure 13B:
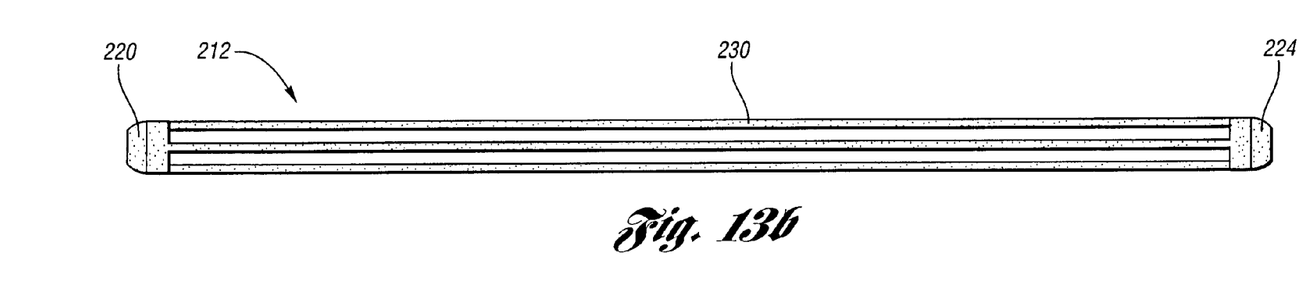
FIG. 13b is a side view of the cutting device depicted in FIG. 10.

FIG. 8 illustrates a flow chart depicting one method 110 for treating a stenotic lesion 18 in a body vessel, implementing the assembly 10 mentioned above. The method 110 comprises percutaneously introducing an expandable balloon 16 at a stenotic lesion 18 in the body vessel in box 112. The method 110 further comprises disposing the integrally formed cutting device 12 having the C-shaped configuration coaxially about the expandable balloon 16 for angioplasty of the stenotic lesion 18 in the body vessel. The method 110 further includes passing saline through the balloon catheter 14 to the expandable balloon 16 to contact the balloon and the device 12 on the stenotic lesion 18. The method 110 further includes inflating the expandable balloon 16 and expanding in box 114 the device 12 for contact with the stenotic lesion 18. The method 110 further comprises fracturing in box 116 the stenotic lesion 18 in the body vessel on each radial plane of fracture with the balloon and the device 12.

FIGS. 9 through 13*b* illustrate an atherosclerosis cutting device and assembly 210 in accordance with another embodiment of the present invention. As shown, the assembly 210 includes similar components as in the assembly 10 depicted in FIGS. 1-3*b* and 7*a* and 7*b*. For example, the wire guide 54, outer catheter 60, and introducer sheath 56 of the assembly 10 in FIGS. 1-2 are similar to the wire guide 254, outer catheter 260, and introducer sheath 256 of the assembly 210 in FIGS. 9-12.

However, in this embodiment, the distal collar 220 and the proximal collar 224 of the cutting device 212 are each formed in the shape of a ring, solidly and integrally, defining a ring configuration relative to an end view. Preferably, the distal and proximal collars 220, 224 include an expandable body 230 integral therefrom. Due to the ring configuration formed on each or both of the collars 220, 224 the device 212 is preferably slid and disposed about the expandable balloon prior to treatment of the stenotic lesion. Thus, during treatment, the device 212 is configured to be percutaneously advanced with the balloon catheter.

Figure 14:
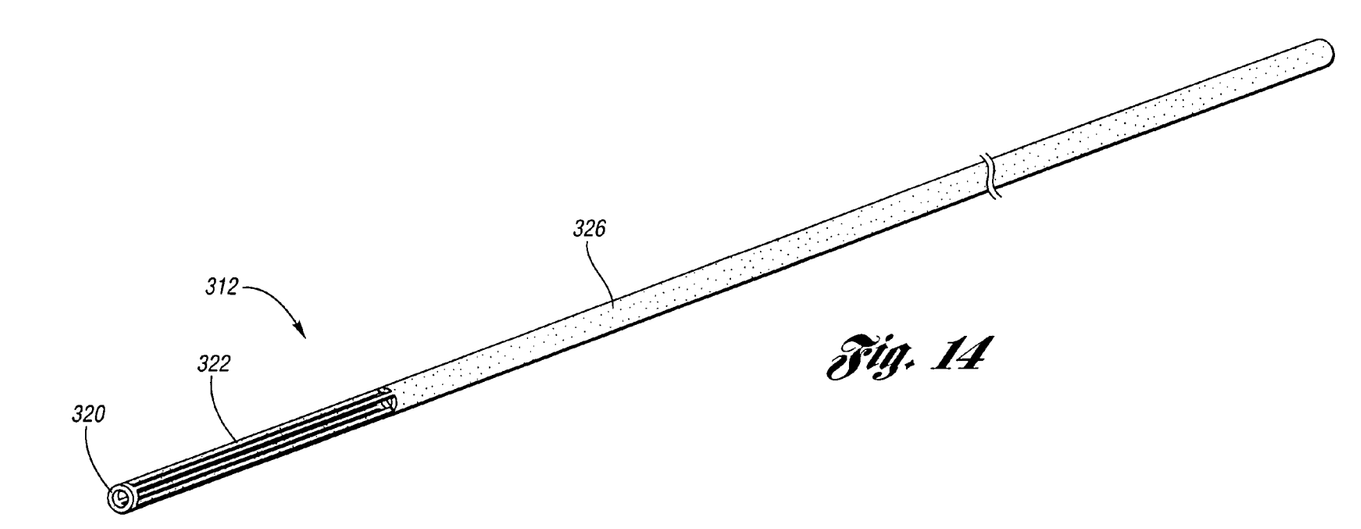
FIG. 14 is a perspective view of an integrally formed cutting device in accordance with another embodiment of the present invention.
Figure 15:
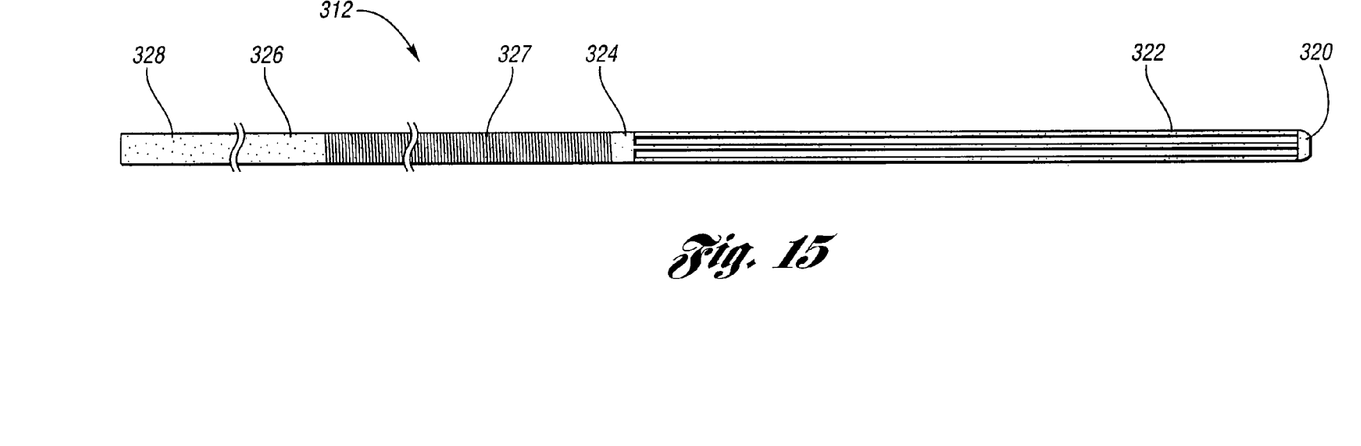
FIG. 15 is a side view of the integrally formed cutting device in FIG. 14.

FIGS. 14 and 15 illustrate an integrally formed atherosclerosis cutting device 312 in accordance with another embodiment of the present invention. As shown, the device 312 includes similar components as in the device 12 depicted in FIGS. 1-3*b* and 7*a* and 7*b*. For example, the distal collar 20, cutting body 22, and the proximal collar 24 of the device 12 in FIGS. 3*a* and 3*b* are similar to the distal collar 320, cutting body 322, and proximal collar 324 in FIGS. 14 and 15. However, in this embodiment, the device 312 further comprises a base member 326 integrally connected with the proximal collar 324 opposite the cutting body 320. As shown, the base member 326 is integrally attached to the proximal collar 324 and extends proximally to a predetermined length. Preferably, the base member is a tubular member integrally formed with the component of the device from a single cannular tube. As mentioned above, this may be achieved by known manufacturing methods such as laser etching or cutting.

In use, the device 312 may be disposed about a balloon catheter having an expandable balloon, such as the balloon catheter mentioned in the assembly above. For treatment of a stenotic lesion, the device may be disposed about the balloon catheter before or after the balloon cather is advanced through an outer catheter for placement at the stenotic lesion in a body vessel. The device 312 in this embodiment provides the medical practitioner with procedural alternatives. For example, in the event it is determined that pre-dilitation, primary dilitation, and post-dilatation stages are advantageous using the same balloon catheter, the device may be selectively used during the primary dilation stage without retracting the balloon catheter from the patient, lessening any risk of potential trauma and shortening the time of procedure. With the length of the base member, the device may be percutaneously introduced and retracted through the body vessel, using the balloon catheter as the guide.

In this embodiment, the base member 326 further may include a distal helical or spiral cut 327 for kink resistance and torque transfer. As shown, the helical cut 327 is formed adjacent the proximal collar 324 and may extend a predetermined length, e.g., between about 80 cm and 130 cm. Referring to FIG. 15, the base member 326 further includes a smooth portion 328 located proximal the distal helical cut 327. As shown, the smooth portion 328 may proximally extend from the distal helical cut 327 for a predetermined length, e.g., between about 5 cm and 25 cm.

The device 12 may be comprised of any suitable material such as a superelastic material, stainless steel wire, cobalt-chromium-nickel-molybdenum-iron alloy, or cobalt-chrome alloy. It is understood that the device 12 may be formed of any other suitable material that will result in a self-opening or self-expanding device, such as shape memory alloys. Shape memory alloys have a property of becoming rigid, that is, returning to a remembered state, when heated above a transition temperature. A shape memory alloy suitable for the present invention may comprise Ni—Ti available under the more commonly known name Nitinol. When this material is heated above the transition temperature, the material undergoes a phase transformation from martensite to austenic, such that material returns to its remembered state. The transition temperature is dependent on the relative proportions of the alloying elements Ni and Ti and the optional inclusion of alloying additives.

In one alternate embodiment, the device 12 may be made from Nitinol with a transition temperature that is slightly below normal body temperature of humans, which is about 98.6° F. Although not necessarily a preferred embodiment, when the device 12 is deployed in a body vessel and exposed to normal body temperature, the alloy of the device 12 will transform to austenite, that is, the remembered state, which for one embodiment of the present invention is the expanded configuration when the device 12 is deployed in the body vessel. To remove the device 12, the device 12 is cooled to transform the material to martensite which is more ductile than austenite, making the device 12 more malleable. As such, the device 12 can be more easily collapsed and pulled into a lumen of a catheter for removal.

In another alternate embodiment, the device 12 may be made from Nitinol with a transition temperature that is above normal body temperature of humans, which is about 98.6° F. Although not necessarily a preferred embodiment, when the device 12 is deployed in a body vessel and exposed to normal body temperature, the device 12 is in the martensitic state so that the device 12 is sufficiently ductile to bend or form into a desired shape, which for the present invention is an expanded configuration. To remove the device 12, the device 12 is heated to transform the alloy to austenite so that the device 12 becomes rigid and returns to a remembered state, which for the device 12 in a collapsed configuration.

While the present invention has been described in terms of preferred embodiments, it will be understood, of course, that the invention is not limited thereto since modifications may be made to those skilled in the art, particularly in light of the foregoing teachings.

The invention claimed is:

1. An angioplasty cutting device for balloon angioplasty of a stenotic lesion on a vessel wall in a body vessel, the device comprising:
 a balloon catheter having a body portion and an expandable balloon attached to the body portion for angioplasty at the stenotic lesion;
 a cutter comprising;
 a distal collar,
 a plurality of struts with the distal collar and proximally extending therefrom, the plurality of struts having a collapsed configuration for delivery or retrieval and an expanded configuration for cutting the stenotic lesion, the plurality of struts defining a cutting body configured to be disposed at the stenotic lesion and to be more radially expandable than the distal collar to engage the stenotic lesion for dilatation of the body vessel during angioplasty, the cutting body extending along and engaging the stenotic lesion generally longitudinally and non-circumferentially, the plurality of struts extending parallel to the longitudinal axis in a collapsed configuration, each strut configured to move along a radial plane of fracture extending from the longitudinal axis to the vessel wall as each struts moves from the collapsed configuration to the expanded configuration; and
 a proximal collar, the plurality of struts being with the proximal collar, at least one of the distal collar and the proximal collar having a slot formed therethrough defining a C-shaped configuration that is configured to be fastened about the expandable balloon; and
 wherein the angioplasty cutting device is removed from the body vessel after engaging the stenotic lesion.

2. The device of claim 1 wherein the cutting body comprises a first portion and a second portion, each first portion being integral with the distal collar and extending longitudinally therefrom to the second portion integral with the proximal collar, the cutting body being radially expandable to engage the stenotic lesion for dilatation of the body vessel during angioplasty.

3. The device of claim 2 wherein the first portion is a distal portion and the second portion is a proximal portion of the plurality of struts.

4. The device of claim 1 wherein the distal and proximal collars and the plurality of struts are formed of a superelastic material, stainless steel, Nitinol, cobalt-chromium-nickel-molybdenum-iron alloy, or cobalt-chrome alloy, or a mixture thereof.

5. The device of claim 1 further comprising a base member integral with the proximal collar for delivery and retrieval of the device in the body vessel.

6. The device of claim 1 wherein the proximal collar has the C-shaped configuration.

7. The device of claim 6 wherein the distal collar has the C-shaped configuration.

8. The device of claim 1 wherein each strut of the plurality of struts has a diameter of between about 0.010 and 0.020 inch.

9. An angioplasty cutting apparatus for treatment of a stenotic lesion on a vessel wall in a body vessel, the device comprising:
 a balloon catheter having a tubular body portion and an expandable balloon attached to and in fluid communication with the tubular body portion for angioplasty at the stenotic lesion, the expandable balloon having distal and proximal portions; and
 a one-piece angioplasty cutting device coaxially adaptable about the expandable balloon for angioplasty of the stenotic lesion in the body vessel, the device comprising:
 a distal collar configured to be disposed adjacent the distal end of the balloon relative to the device;
 a cutting body including a plurality of struts, the plurality of struts having a collapsed configuration for delivery or retrieval and an expanded configuration for cutting the stenotic lesion, each strut having a first portion and a second portion, each first portion being with the distal collar and extending longitudinally therefrom to the second portion, the cutting body being more radially expandable than the distal collar with the balloon to engage the stenotic lesion for dilatation of the body vessel during angioplasty, the cutting body extending along and engaging the stenotic lesion generally longitudinally and non-circumferentially, the plurality of struts extending parallel to the longitudinal axis in a collapsed configuration, each strut configured to move along a radial plane of fracture extending from the longitudinal axis to the vessel wall as each strut moves from the collapsed configuration to the expanded configuration; and a proximal collar configured to be disposed adjacent the proximal end of the balloon relative to the device, each second portion being with the proximal collar, and at least one of the distal collar and the proximal collar has a slot formed therethrough defining a C-shaped configuration that is configured to be fastened about the expandable balloon, the at least one of the collars attaching to the balloon catheter at one of the distal portion and proximal portion thereof; and wherein the angioplasty cutting apparatus is removed from the body vessel after engaging the stenotic lesion.

10. The apparatus of claim 9 wherein the device further includes a base member integral with the proximal collar for delivery and retrieval of the device in the body vessel.

11. The apparatus of claim 9 further comprising:

an inner catheter having a distal end through which the balloon catheter is disposed for delivery of the device in the body vessel;

a wire guide configured to be disposed through the inner lumen of the balloon catheter for percutaneous guidance through the body vessel; and an introducer sheath through which the inner catheter is inserted for percutaneous insertion to the body vessel.

12. The apparatus of claim 11 wherein the balloon catheter further includes a proximal end, the proximal end having a hub in fluid communication with the expandable balloon for fluid to be passed therethrough for inflation and deflation of the balloon during angioplasty.

13. The apparatus of claim 9 wherein the distal and proximal collars and the struts are formed of a superelastic material, stainless steel, Nitinol, cobalt-chromium-nickel-molybdenum-iron alloy, or cobalt-chrome alloy, or a mixture thereof.

14. The device of claim 1, wherein both the proximal collar and the distal collar have a slot formed therethrough forming a C-shaped configuration, the slots being radially aligned with each other along the circumferences of the proximal and distal collars.

15. The device of claim 1, wherein the device is free of circumferentially extending cutting rings.

16. The apparatus of claim 9, wherein the device is free of circumferentially extending cutting rings.

17. The device of claim 1 wherein each of the distal collar and the proximal collar has a constant outer diameter along the longitudinal axis.

18. The device of claim 1 wherein a radial distance between the longitudinal axis and at least one of the struts in the collapsed configuration is at least the radius of the proximal collar and the distal collar.

\* \* \* \* \*